US011389195B2

(12) United States Patent
Marshall

(10) Patent No.: US 11,389,195 B2
(45) Date of Patent: Jul. 19, 2022

(54) IMPLANT TOOLS FOR EXTRA VASCULAR IMPLANTATION OF MEDICAL LEADS

(71) Applicant: Medtronic, Inc., Minneapolis, MN (US)

(72) Inventor: Mark T. Marshall, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/163,413

(22) Filed: Jan. 24, 2014

(65) Prior Publication Data

US 2015/0209077 A1 Jul. 30, 2015

(51) Int. Cl.
*A61B 17/34* (2006.01)
*A61N 1/372* (2006.01)
(Continued)

(52) U.S. Cl.
CPC ...... *A61B 17/3468* (2013.01); *A61B 17/3417* (2013.01); *A61N 1/372* (2013.01);
(Continued)

(58) Field of Classification Search
CPC ............ A61B 17/3468; A61B 17/3417; A61B 2017/003; A61B 2017/00323; A61B 17/32053; A61B 17/3403; A61B 17/347; A61B 2017/347; A61B 2017/00318; A61B 2017/00327; A61B 2017/00331; A61N 1/372; A61N 1/056; A61N 1/0587–0597; A61M 29/00–2029/025; A61M 39/0247; A61M 2005/1581; A61M 2025/0004; A61M 2025/0006; A61M 2025/0086; A61M 2025/009; A61M 25/0136
(Continued)

(56) References Cited

U.S. PATENT DOCUMENTS 3,506,007 A * 4/1970 Henkin ............... A61B 17/3401
604/165.01
3,941,127 A * 3/1976 Froning ............. A61B 17/3401
604/506
(Continued)

FOREIGN PATENT DOCUMENTS

EP 1990069 A1 11/2008

*Primary Examiner* — Tan-Uyen T Ho
*Assistant Examiner* — Charles M Wei
(74) *Attorney, Agent, or Firm* — Christopher & Weisberg, P.A.

(57) ABSTRACT

A method for creating a pathway for insertion of a medical lead, such as a defibrillation lead, the method includes creating an incision at a first location on the left side of the torso of the patient. A first medical device and a second medical device are advanced through the incision and through the subcutaneous tissue toward a second location proximate the center of the torso. The distal end of the first medical device is deflected at the second location toward a third location proximate the high sternal area. The second medical device is advanced out through the distal end of the first medical device toward the third location. A sheath is positioned within the torso, the sheath spanning the distance between the first location and the second location and the distance between the second location and the third location.

8 Claims, 10 Drawing Sheets

(51) Int. Cl.
  *A61N 1/05* (2006.01)
  *A61N 1/39* (2006.01)
  *A61B 17/00* (2006.01)

(52) U.S. Cl.
  CPC .................. *A61B 2017/003* (2013.01); *A61B 2017/00323* (2013.01); *A61N 1/05* (2013.01); *A61N 1/0504* (2013.01); *A61N 1/0592* (2013.01); *A61N 1/3956* (2013.01)

(58) Field of Classification Search
  USPC .............................................. 606/129; 607/5
  See application file for complete search history.

(56) References Cited

U.S. PATENT DOCUMENTS

| | | | | |
|---|---|---|---|---|
| 4,013,080 A | * | 3/1977 | Froning | A61B 17/3401 604/165.01 |
| 4,471,777 A | * | 9/1984 | McCorkle, Jr. | A61B 17/221 294/100 |
| 4,757,827 A | * | 7/1988 | Buchbinder | A61M 25/0136 600/434 |
| 4,790,830 A | * | 12/1988 | Hamacher | A61M 5/32 604/239 |
| 4,863,430 A | * | 9/1989 | Klyce | A61B 17/3421 604/170.03 |
| 5,123,910 A | * | 6/1992 | McIntosh | A61B 17/06066 606/223 |
| 5,282,845 A | * | 2/1994 | Bush | A61N 1/0587 607/127 |
| 5,300,106 A | * | 4/1994 | Dahl | A61N 1/05 604/164.05 |
| 5,322,064 A | * | 6/1994 | Lundquist | A61B 18/1492 600/381 |
| 5,395,329 A | * | 3/1995 | Fleischhacker | A61M 25/0147 604/95.04 |
| 5,437,288 A | * | 8/1995 | Schwartz | A61M 25/09 600/434 |
| 5,439,006 A | * | 8/1995 | Brennen | A61M 25/0136 600/434 |
| 5,573,511 A | * | 11/1996 | Yoon | A61B 17/3417 604/164.12 |
| 5,702,365 A | * | 12/1997 | King | A61M 29/02 604/105 |
| 5,868,729 A | * | 2/1999 | Pelfrey | A61F 2/26 600/38 |
| 6,042,576 A | * | 3/2000 | DeVries | A61M 25/007 604/264 |
| 6,045,532 A | * | 4/2000 | Eggers | A61B 18/1482 604/114 |
| 6,063,098 A | * | 5/2000 | Houser | A61B 17/22012 606/169 |
| 6,093,173 A | * | 7/2000 | Balceta | A61M 29/02 604/104 |
| 6,641,564 B1 | * | 11/2003 | Kraus | A61B 17/3415 604/110 |
| 6,656,195 B2 | | 12/2003 | Peters et al. | |
| 7,274,962 B2 | * | 9/2007 | Bardy | A61N 1/05 600/377 |
| 7,695,512 B2 | | 4/2010 | Lashinski et al. | |
| 8,409,236 B2 | * | 4/2013 | Pillai | A61M 39/0247 606/170 |
| 2003/0093104 A1 | * | 5/2003 | Bonner | A61B 17/3478 606/185 |
| 2005/0234294 A1 | * | 10/2005 | Saadat | A61B 1/0008 600/104 |
| 2007/0016131 A1 | * | 1/2007 | Munger | A61M 25/0127 604/95.05 |
| 2007/0162101 A1 | | 7/2007 | Burgermeister et al. | |
| 2008/0262430 A1 | * | 10/2008 | Anderson | A61B 17/3415 604/164.1 |
| 2009/0275972 A1 | * | 11/2009 | Uemura | A61B 17/0401 606/192 |
| 2010/0099952 A1 | | 4/2010 | Adams | |
| 2010/0137879 A1 | | 6/2010 | Ko et al. | |
| 2010/0318098 A1 | | 12/2010 | Lund et al. | |
| 2011/0144690 A1 | * | 6/2011 | Bishop | A61F 2/2433 606/195 |
| 2011/0264011 A1 | | 10/2011 | Wu et al. | |
| 2014/0350417 A1 | * | 11/2014 | Van Bladel | A61B 5/0215 600/486 |

\* cited by examiner

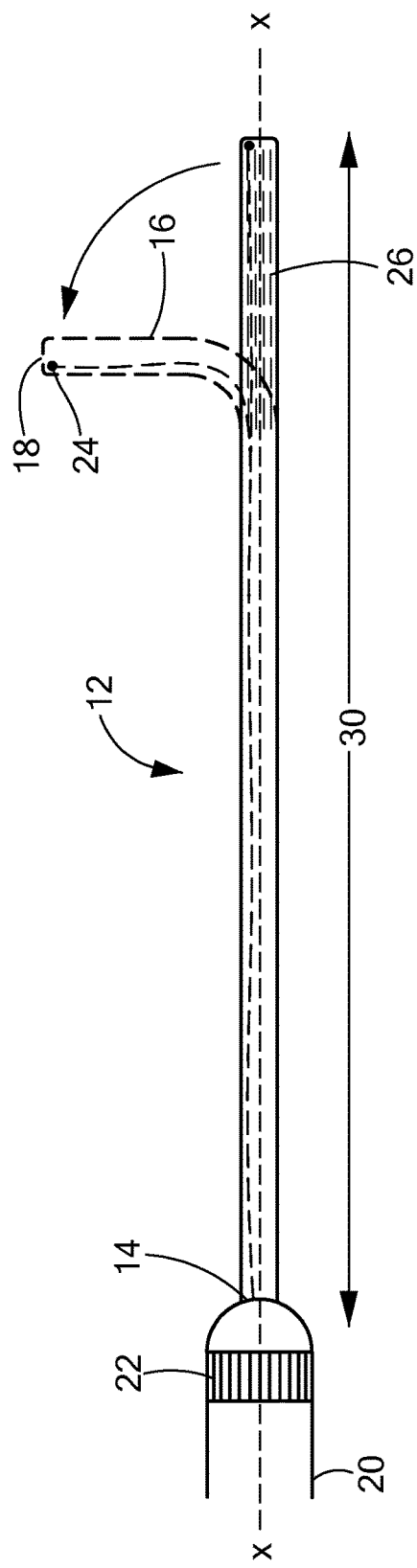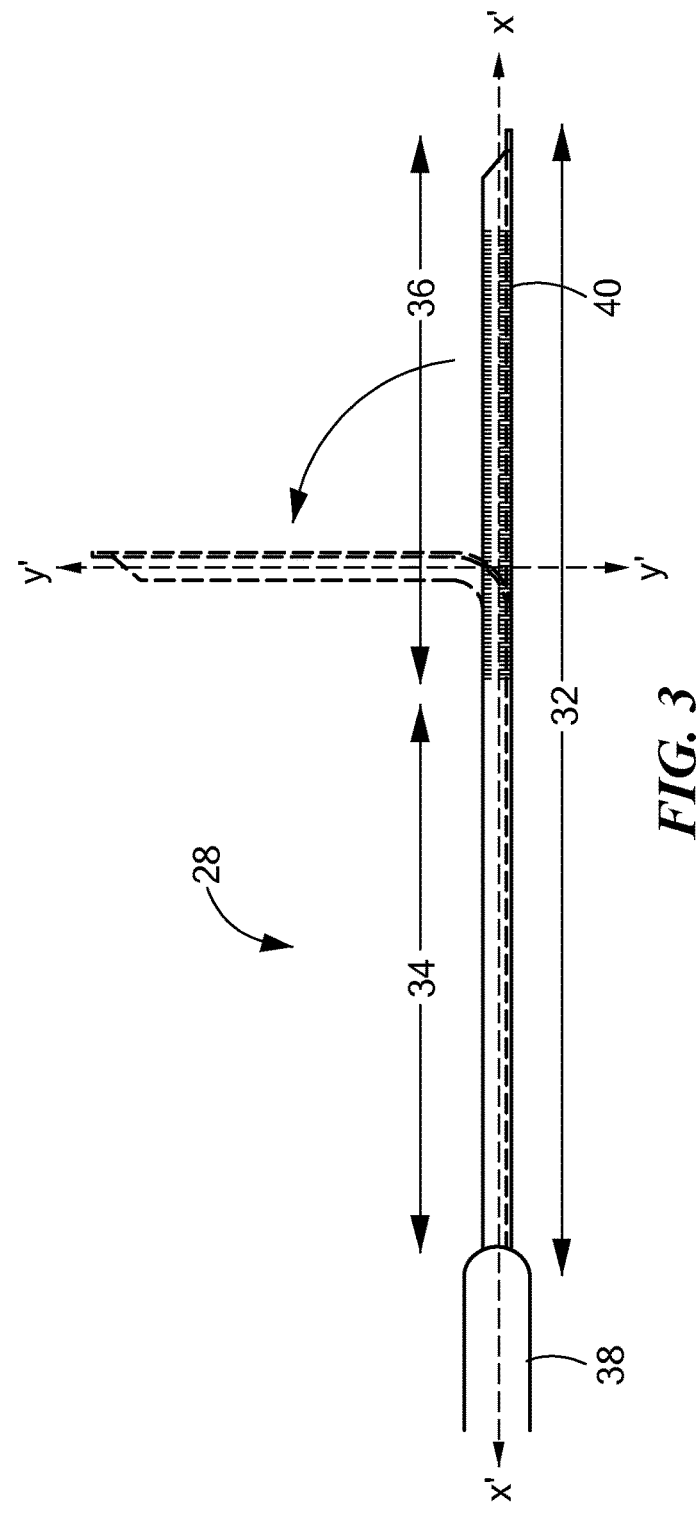
FIG. 2
FIG. 3

IMPLANT TOOLS FOR EXTRA VASCULAR IMPLANTATION OF MEDICAL LEADS

CROSS-REFERENCE TO RELATED APPLICATION n/a

STATEMENT REGARDING FEDERALLY SPONSORED RESEARCH OR DEVELOPMENT n/a

FIELD OF THE INVENTION

The present application relates to a method and system for extravascular implantation of a medical lead.

BACKGROUND OF THE INVENTION

Malignant tachyarrhythmia, for example, atrial or ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients at high risk of ventricular fibrillation, the use of an implantable cardioverter defibrillator (ICD) system has been shown to be beneficial at preventing SCD. An ICD system includes an ICD, which is a small battery powered electrical shock device, may include an electrical housing, or can electrode, that is coupled to one or more electrical lead wires placed within the heart. If an arrhythmia is sensed, the ICD may send a pulse via the electrical lead wires to shock the heart and restore its normal rhythm. Owing to the inherent surgical risks in attaching and replacing electrical leads directly within or on the heart, methods have been devised to achieve a similar effect to that of a transvenous ICD system connected directly to heart without placing electrical lead wires within the heart or attaching electrical wires directly to the heart.

Subcutaneous implantable cardioverter-defibrillator (SubQ ICD) systems have been devised to deliver electrical impulses to the heart by the use of a defibrillation lead placed subcutaneously on the torso. In order to effectively electrically stimulate the heart, the distal end of the defibrillation lead may be oriented longitudinally spanning from approximately the xiphoid to the high sternal area. However current methods of positioning the defibrillation lead in the proper position often include making as many as three incision points on the patient's torso, which increases the risk of infection, complexity of the procedure, surgical duration, and cost. In particular, current methods of implanting a subcutaneous lead include making an incision at the patient's left torso, xiphoid, and higher sternal area. Accordingly, it is desirable to reduce the number of incisions to reduce the rate of infection, complexity, the invasiveness of the procedure, and cost.

SUMMARY

The present invention advantageously provides a method and system for creating a pathway for insertion of a medical lead, such as a defibrillation lead, the method includes creating an incision at a first location on the left side of the torso of the patient. A first medical device and a second medical device are advanced through the incision and through the subcutaneous tissue toward a second location proximate the center of the torso. The distal end of the first medical device is deflected at the second location toward a third location proximate the high sternal area. The second medical device is advanced out through the distal end of the first medical device toward the third location. A sheath is positioned within the torso, the sheath spanning the distance between the first location and the second location and the distance between the second location and the third location.

In another embodiment, the system includes a first medical device having a proximal end, a distal end, and a lumen there through, the distal end of the first medical device being deflectable. A second medical device is slideably receivable within the lumen of the first medical device, the second medical device having a proximal portion, a distal portion, and a major axis. The distal portion of the second medical device is slideable out through the distal end of the first medical device, the distal end of the second medical device extending longitudinally at an angle substantially orthogonal to the major axis when the distal end of the first medical device is deflected and the distal portion of the second medical device is slid out through the distal end of the first medical device.

In yet another embodiment, the method includes creating an incision at a first location on the left side of the torso of the patient. A first medical device and a second medical device are advanced through the incision and through the subcutaneous tissue toward a second location proximate the center of the torso. The distal end of the first medical device is deflected at the second location toward a third location proximate the high sternal area. The distal portion of the second medical device is advanced out through the distal end of the first medical device toward the third location, the distal portion of the second medical device having a plurality of electrodes. When the distal end of the first medical device is deflected the distal portion of the of the second medical device bends to an angle of approximately 90 degrees with respect to the proximal portion of the second medical device. The first medical device defines a first length and the second medical device defines a second length, and wherein the second length is longer than the first length. A sheath is positioned within the torso, the sheath spanning the distance between the first location and the second location and the distance between the second location and the third location. The defibrillation lead is advanced through the sheath and positioning the defibrillation lead between the second location and the third location. A subcutaneous pocket is created proximate the incision, the pocket sized to retain an implantable cardioverter-defibrillator having a can electrode. The proximal end of the defibrillation lead is electrically connected to the can electrode.

BRIEF DESCRIPTION OF THE DRAWINGS

A more complete understanding of the present application, and the attendant advantages and features thereof, will be more readily understood by reference to the following detailed description when considered in conjunction with the accompanying drawings wherein:

FIG. 2 is a side cross-sectional view of the first medical device shown in FIG. 1;

FIG. 3 is a side cross-sectional view of a second medical device constructed in accordance with the principles of the present application;

DETAILED DESCRIPTION OF THE INVENTION

Figure 1:
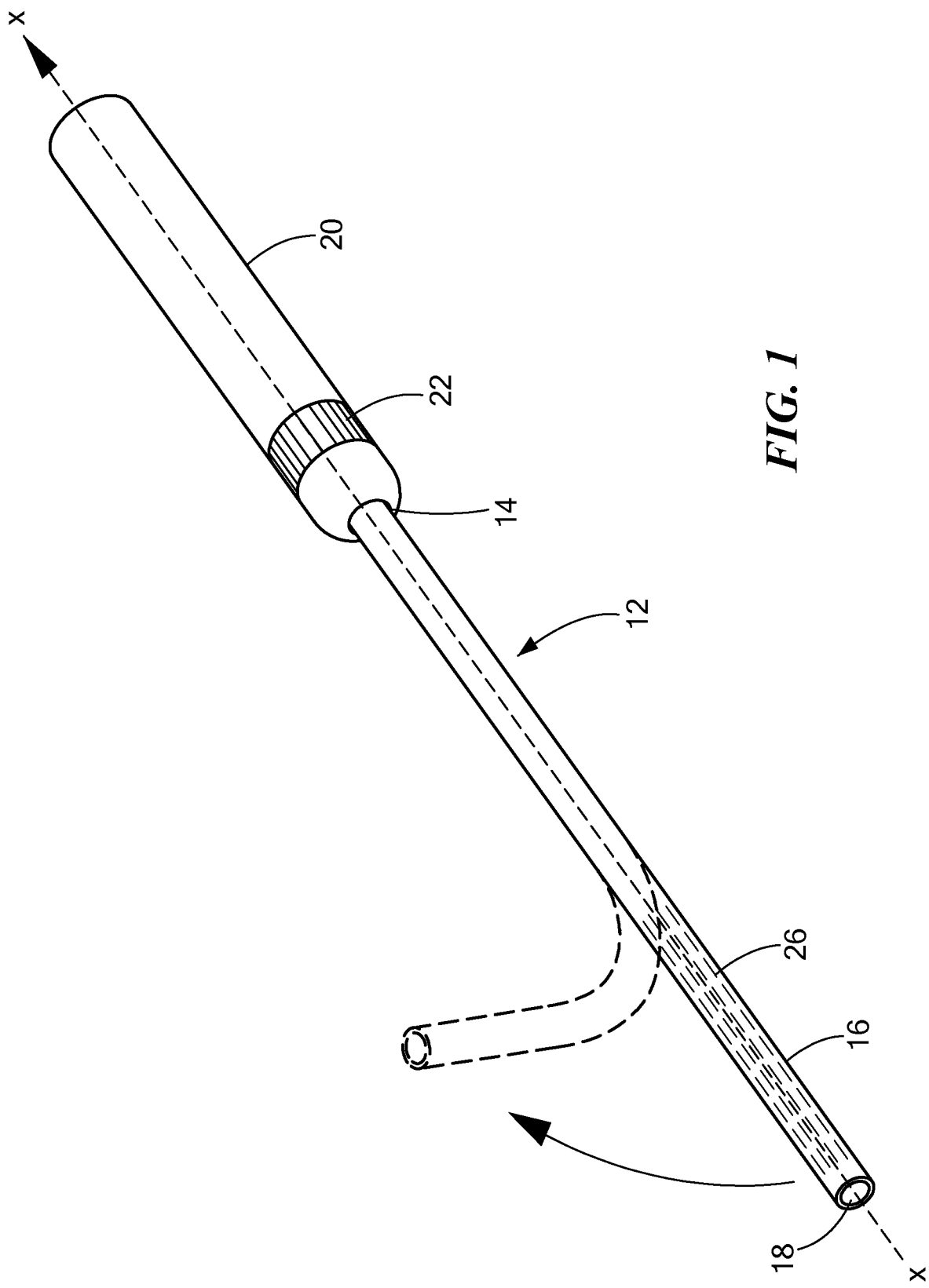
FIG. 1 is a perspective view of a first medical device constructed in accordance with the principles of the present application.

Now referring to the drawings in which like reference designators refer to like elements, there is shown in a medical system 10 for creating a pathway within a patient for extravascular implantation of a medical lead, such as a defibrillation lead. Referring now to FIGS. 1 and 2, the system 10 may include a first medical device 12 sized to be received within an animal or human patient. The first medical device 12 may be a medical catheter, or other similarly sized device, that may be advanced through the subcutaneous tissue of a patient's torso or through the vasculature.

The first medical device 12 may include a proximal end 14, a distal end 16, and a lumen 18 there through. The first medical device 12 may include a handle 20 coupled to the proximal end 14 and an actuator 22 mechanical coupled to a pull wire or other actuation element 24 (seen in FIG. 2) configured deflect the distal end 16 of the medical device 12. For example, the actuator 22 may be a rotatable collar included on the handle 20. When the rotatable collar is rotated in a predetermined direction, the actuation element 24, for example, a pull wire, may pull on the distal end 16 of the medical device 12 causing it to deflect in a desired direction. In an exemplary configuration, the pull wire may be positioned on one side of the first medical device 12 to facilitate deflection of the distal end 16 in the direction of that side. The actuator 22 may be realized using mechanisms other than the rotatable collar, such as mechanically actuated triggers, levers, or other mechanisms known in the art. Likewise, the actuation element 24 may be realized using other mechanisms well known in the art.

In an exemplary configuration, the distal end 16 of the first medical device 12 is deflectable to any number of configurations including up to angles of 90 degrees or greater with respect to a major axis "x" defined by the first medical device 12. The distal end 16 may further define any shape when deflected, for example, linear, curvilinear, or helical. The distal end 16 of the medical device 12 may define a first plurality of slits 26, for example, laser cut slits, to facilitate the deflection of the distal end 16. Any number of slits 26 may be disposed on the distal end 16 of the first medical device 12 sufficient to facilitate the deflection of the distal end 16. In particular, the slits 26 may be disposed along the entirety, or substantially the entirety, of the deflectable portion of the distal end 16. The slits 26 may be disposed around a portion of the circumference of the first medical device 12, or in a helical pattern, or alternatively, on a single side of the distal end 16 such that the distal end 16 deflects in a single direction. The slits 26 may be defined such that they extend medially along the exterior of the first medical device 12 in a circumferential or helical geometry, from opposite sides of the medical device 12, while leaving a center portion of the first medical device 12 uncut, which may facilitate the deflection of the first medical device 12 more than one direction. Indicia may be included on the handle 20 to indicate the extent and direction of the deflection of the distal end 16. In other configurations not including the slits 26, the first medical device 12 may be composed of a flexible shape memory material, for example, a nickel titanium alloy, that enables the distal end 16 of the first medical device 12 to bend and retain its shape.

Referring now to FIG. 3, slideably receivable within the lumen 18 is a second medical device 28. The second medical device 28 may be sized to slide into the proximal end 14 and out the distal end 16 of the first medical device 12. In particular, the diameter of the lumen 18 may be larger than the diameter of the exterior of the second medical device 28 to enable to second medical device 28 to be slideably inserted within the lumen 18. The first medical device 12 may define a first length 30, and the second medical device 28 may define a second length 32, the second length 32 may be longer than the first length 30 such that the second medical device 32 may extend beyond the distal end 16 of the first medical device. Alternatively, the first length 30 and the second length 32 may the same or the first length 30 may be longer than the second length 32.

The second medical device 28 may be a tunnel creating tool, such as an obturator, a stiff coil structure configured to withstand compressive loading, or a hypotube, configured to dissect or otherwise tunnel through the subcutaneous tissue of the patient's torso. For example, the second medical device 28 may be configured with a sharp edge around at least a portion of its exterior and may define a substantially U-Shaped or V-shaped cross-section to facilitate the ability of the second medical device 28 to tunnel through a portion of the subcutaneous tissue of the patient's torso. The second medical device 28 may have a proximal portion 34 and a distal portion 36 that span the second length 32. The proximal portion 34 may be coupled to a second handle 38 and the distal end of distal portion 36 may define a beveled edge to facilitate the tunneling through subcutaneous tissue. Alternatively, the distal end of the distal portion 36 may include a blunt tip to facilitate atraumatic dissection of tissue as it is advanced through the subcutaneous tissue. In other configurations, the second medical device 28 may be an electrosurgical tool configured to ablate subcutaneous tissue while minimizing bleeding. For example, the distal end 16 of the distal portion 36 may include a conductive element (not shown) configured to freeze or burn tissue as it is advanced. In this configuration, the conductive element may be ultrasonically powered to facilitate movement of the distal end 16 through adipose tissue.

The distal portion 36 of the second medical device 28 may define a second plurality of slits 40 spanning at least substantially the entirety of the distal portion 36. The second plurality of slits 40 may be laser or mechanically cut into the distal portion 36, which may span from approximately the mid-point of the second length 32, or any from any location, be in the same of similar manner to that of the slits 26 to provide flexibility to the distal portion 36. In an exemplary configuration, as discussed in more detail below, the distal portion 36 may be forced or otherwise deflected to define a substantially rigid column. For example, the second medical device 28 may define a major axis "x'." When a force is applied to the second medical device 28 in a direction "y'" substantially orthogonal to the major axis x', the distal portion 36 may align in a position at least substantially orthogonal to the major axis x' as deflected by the first medical device 12. The second plurality of slits 40 may be included along the distal portion 36 and arranged in such a manner that facilitates the bending of the distal portion 36 to define the substantially rigid longitudinal column when the distal portion 36 is slid out the distal end 16 of the first medical device 12. For example, the slits 40 may be defined in the distal portion 26 such that axial compression on the distal portion 26 does not cause the distal portion to deflect.

The slits 40 may further be arranged such that the second distal portion 36 may dissect subcutaneous tissue in a longitudinal direction substantially parallel with the direction y' while bending or otherwise swinging from an orientation substantially parallel to the major axis x' to an orientation substantially orthogonal to the major axis x'. In particular, the distal portion 36 may be sufficiently sharp to slice through the subcutaneous tissue of the torso while extending superiorly toward the higher sternal area without being deflected or otherwise dislodged by the subcutaneous tissue.

Figure 4:
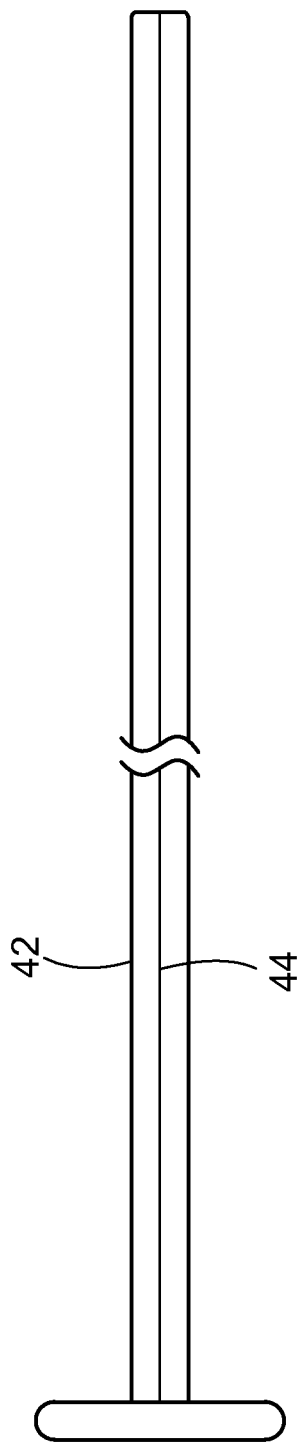
FIG. 4 is a side cross-sectional view of a sheath constructed in accordance with the principles of the present application.

Referring now to FIG. 4, a sheath 42 may be included with the system 10 slideably disposable about the first medical device 12 and the second medical device 28. The sheath 42 may be any sterile device known in the art that facilitates the advancement and removal of medical devices from the patient. In an exemplary configuration, the sheath 42 is kink resistant and may be splittable/slittable along its major axis. For example, the sheath 42 may include a long score 44 along its major axis allows the sheath to be torn or otherwise peeled off when being removed from the torso of the patient while leaving an inserted medical device or instrument in place.

Figure 5:
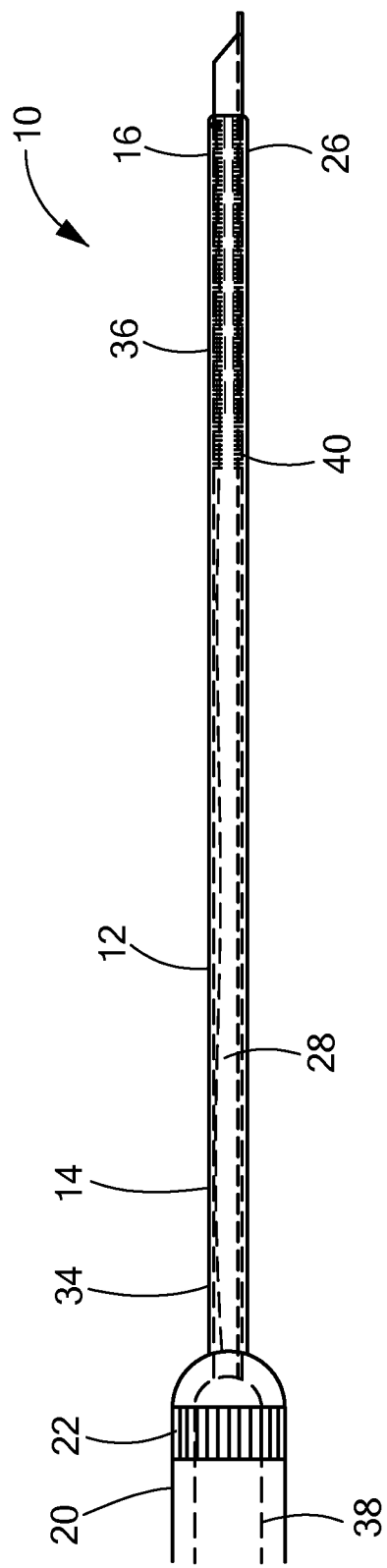
FIG. 5 is a side cross-sectional view of the second medical device shown in FIG. 3 disposed within the first medical device shown in FIG. 1.
Figure 6:
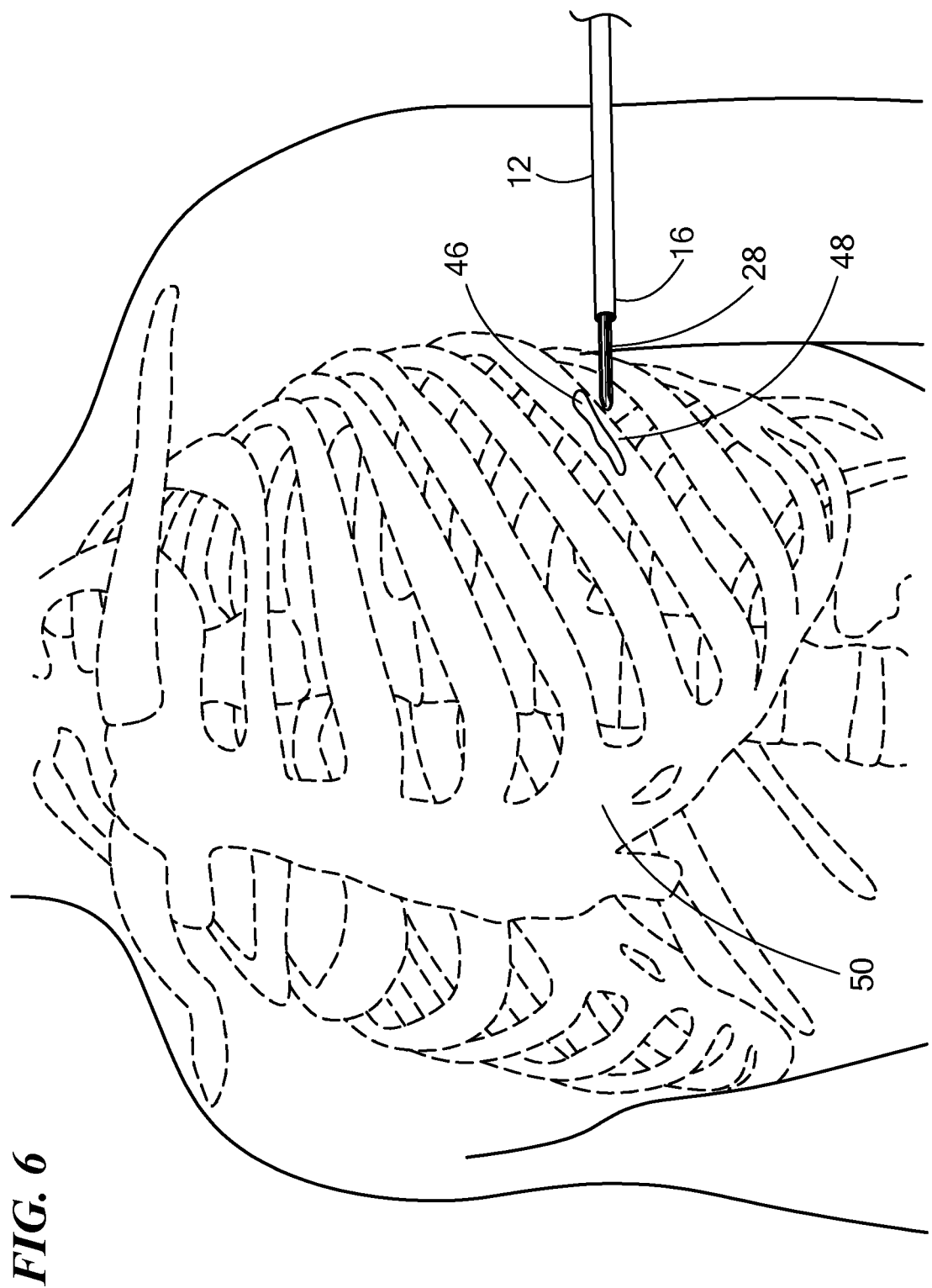
FIG. 6 is a front view of the first medical device and the second medical device shown in FIG. 5 proximate an incision at a first location of a human torso.
Figure 7:
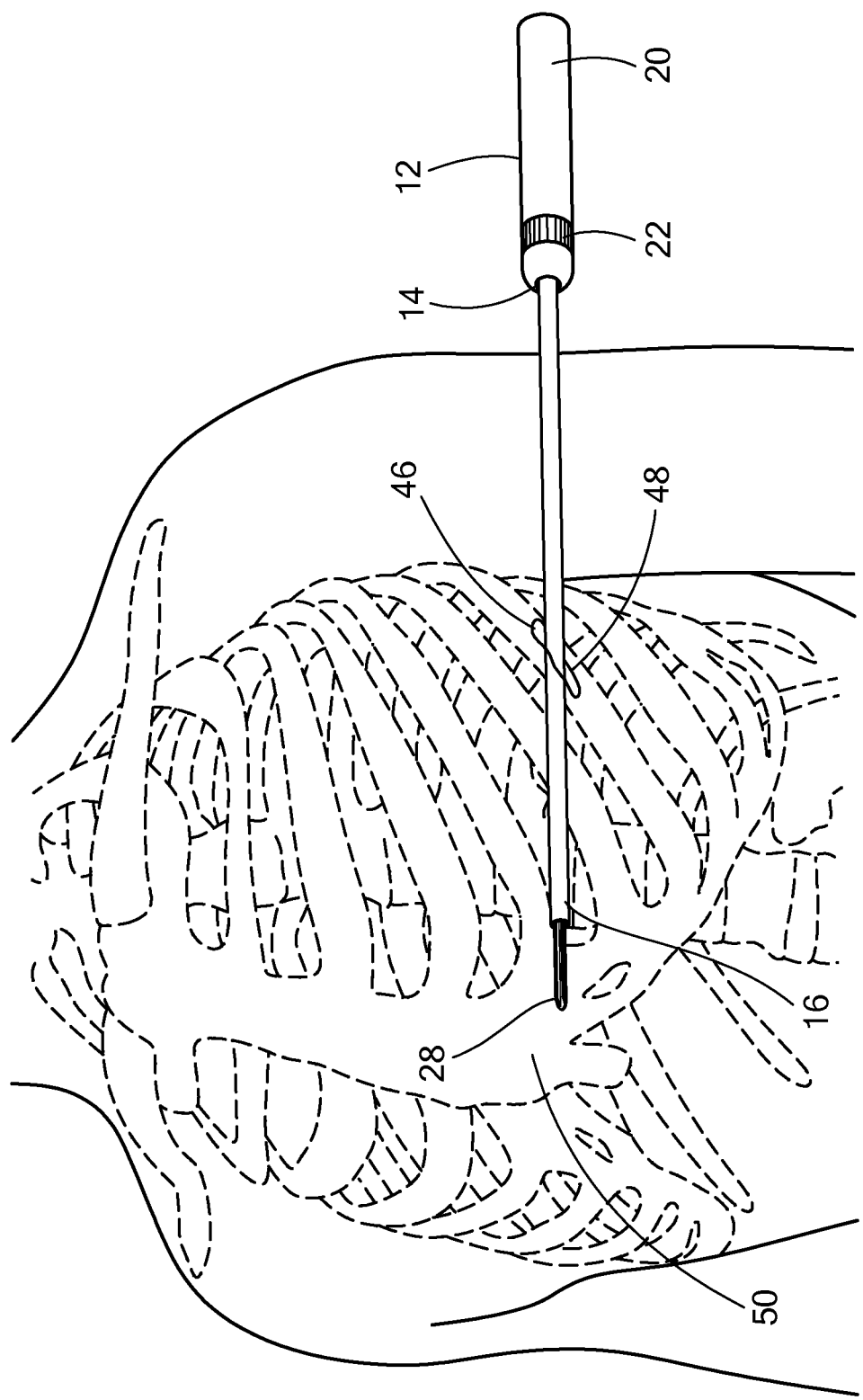
FIG. 7 is a front view of the first medical device and the second medical device shown in FIG. 6 advanced with the human torso to a second location proximate the xiphoid.

Referring now to FIGS. 5-7, in an exemplary use of the system 10, a surgeon may make an incision 46 on the left or right side of the patient's torso. In an exemplary method, the surgeon makes the incision 46 on the left side of the torso at a first location 48 at approximately the fifth or sixth rib proximate the armpit. The first medical device 12 and the second medical device 28 may then be inserted at the first location 48 (FIG. 6) and advanced toward the center of the torso to a second location 50 proximate the xiphoid (FIG. 7). The second medical device 28 may protrude a distance away from the distal end 16 of the first medical device 12 as the first medical device 12 and the second medical device 28 are advanced substantially simultaneously toward the second location 50 to facilitate the tunneling through the subcutaneous tissue.

Alternatively, the second medical device 28 may be advanced first from the first location 48 to the second location 50 followed sequentially by the first medical device 12. The first medical device 12 and the second medical device 28 may be advanced at least substantially parallel to the major axes x and x' along the patients torso toward the second location 50. Alternatively, the first medical device 12 and the second medical device 28 may create any pathway, in any direction, from the first location 48 to the second location 50 depending on the position of the first location 48.

Figure 8:
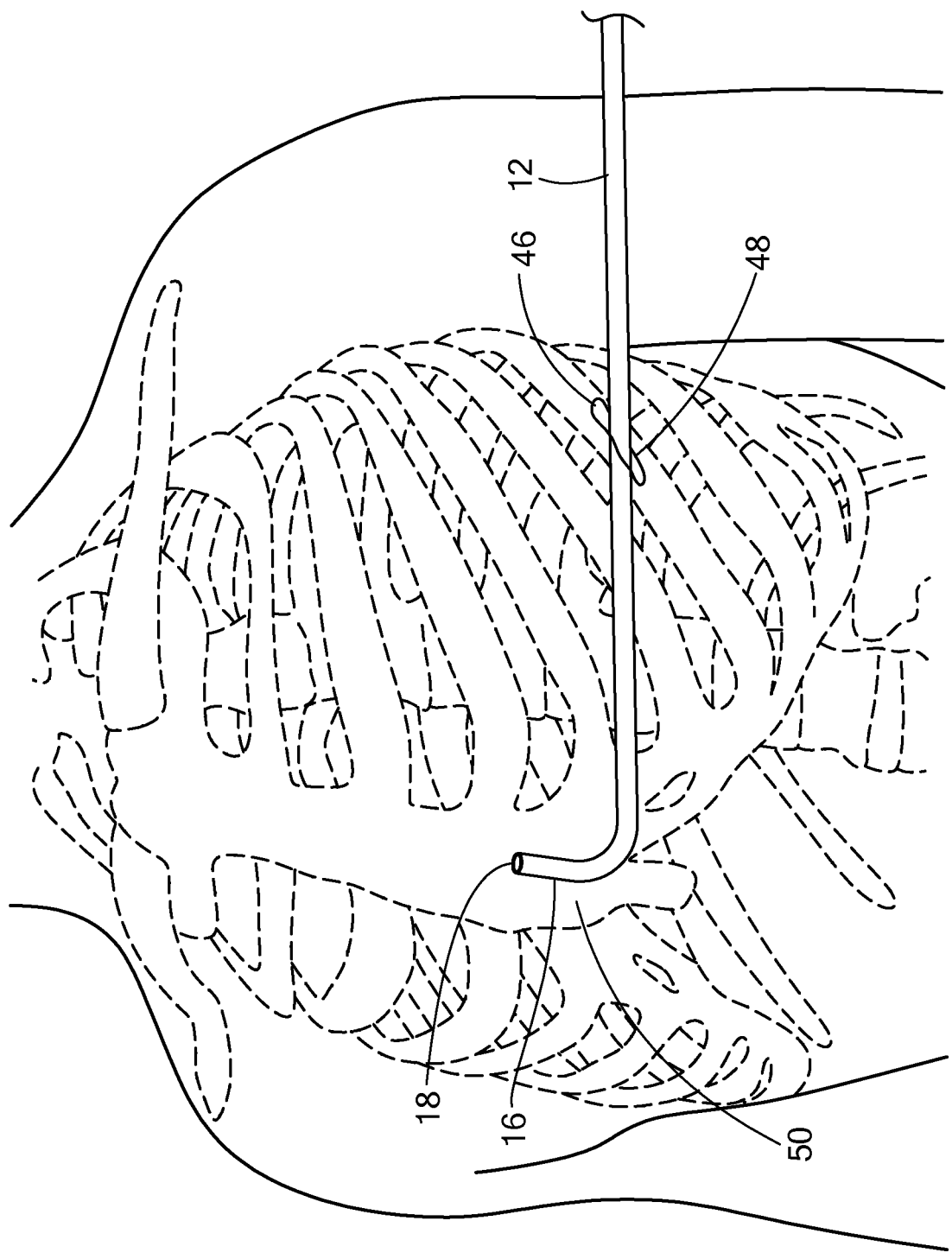
FIG. 8 is a front view of the first medical device and the second medical device shown in FIG. 7 with the distal end of the first medical device deflected in the direction of a third location.

Referring now to FIG. 8, when the first medical device 12 and the second medical device 28 are positioned proximate the second location 48, the actuator 22 may be rotated or otherwise actuated to deflect the distal end 16 of the first medical device 12 toward a third location 52, proximate the high sternal area. To facilitate the proper angle of deflection of the distal 16 end to advance the second medical device 28 toward the third location 52, the actuator 22, and associated actuation element 24, may be configured with a maximum deflection radius. For example, a complete rotation of the actuator may result in the distal end 16 bending to an angle of approximately 90 degrees with respect to the major axis x. Optionally, the actuator 22 may include suitable indicia, (for example, 10 degrees, 20 degrees, etc., or an indication of direction, for example, upward, downward, inward, etc.) to provide the surgeon with the precise angle of deflection of the distal end 16 to enable to the surgeon to create a non-orthogonal pathway to the third location 52.

In an exemplary configuration, the distal end of the distal portion 36 may be substantially co-terminus with the distal end 16 of the first medical device 12 proximate the second location 50. The distal end 16 of the first medical device 12 may then be slid past the distal end of the distal portion 36 and, sequentially or simultaneously, deflected in the direction of the third location 52. In particular, the distal end 16 may be deflected in a direction substantially orthogonal to the major axes x and x'. Alternatively, the distal portion 36 may be advanced farther than the distal end 16 of the first medical device 12 (as shown in FIG. 7) as the first medical device 12 and the second medical device 28 are advanced toward the second location 50. In this configuration, the distal portion 36 may extend a distance away from the distal end 16. When the distal end 16 of the first medical device 12 is deflected, the distal portion 36 is pulled along with the distal end 16 to a position substantially orthogonal to the axes x and x'. As the distal portion 36 is pulled by the distal end 16 it may dissect subcutaneous tissue.

Figure 9:
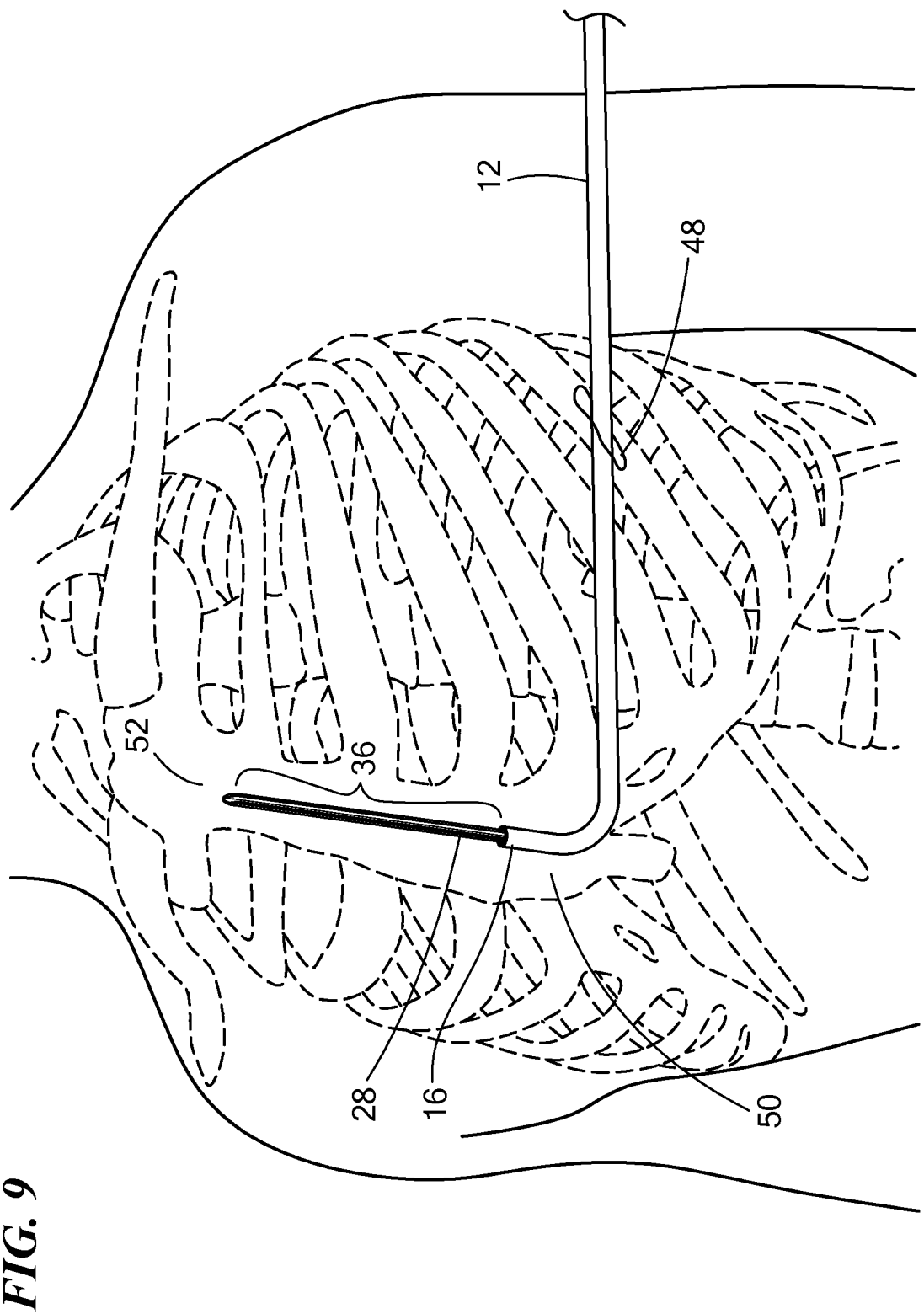
FIG. 9 is a front view of the first medical device and the second medical device shown in FIG. 8 with the second medical device advanced toward the third location proximate the higher sternal area.

Referring now to FIG. 9, the distal portion 36 of the second medical device 28 may be advanced in a longitudinal direction, or along any pathway, from the second location 50 to the third location 52. Owing to the slits 40, the distal portion 36 may be substantially rigid as it is advanced from the second location 50 to the third location 52. That is, as the distal portion 36 is slid out the distal end 16 it forms a substantially longitudinal and rigid column that dissects subcutaneous tissue as it is advanced toward the third location 52. The third location 52 may be proximate the first or second rib in the upper sternum area such that the distal portion 36 of the second medical device 28 lies substantially perpendicular to the sternum underneath the skin and offset to the left of the sternum. In other configurations, the second medical device 28 may lie offset to the right of the sternum or directly over the sternum.

Figure 10:
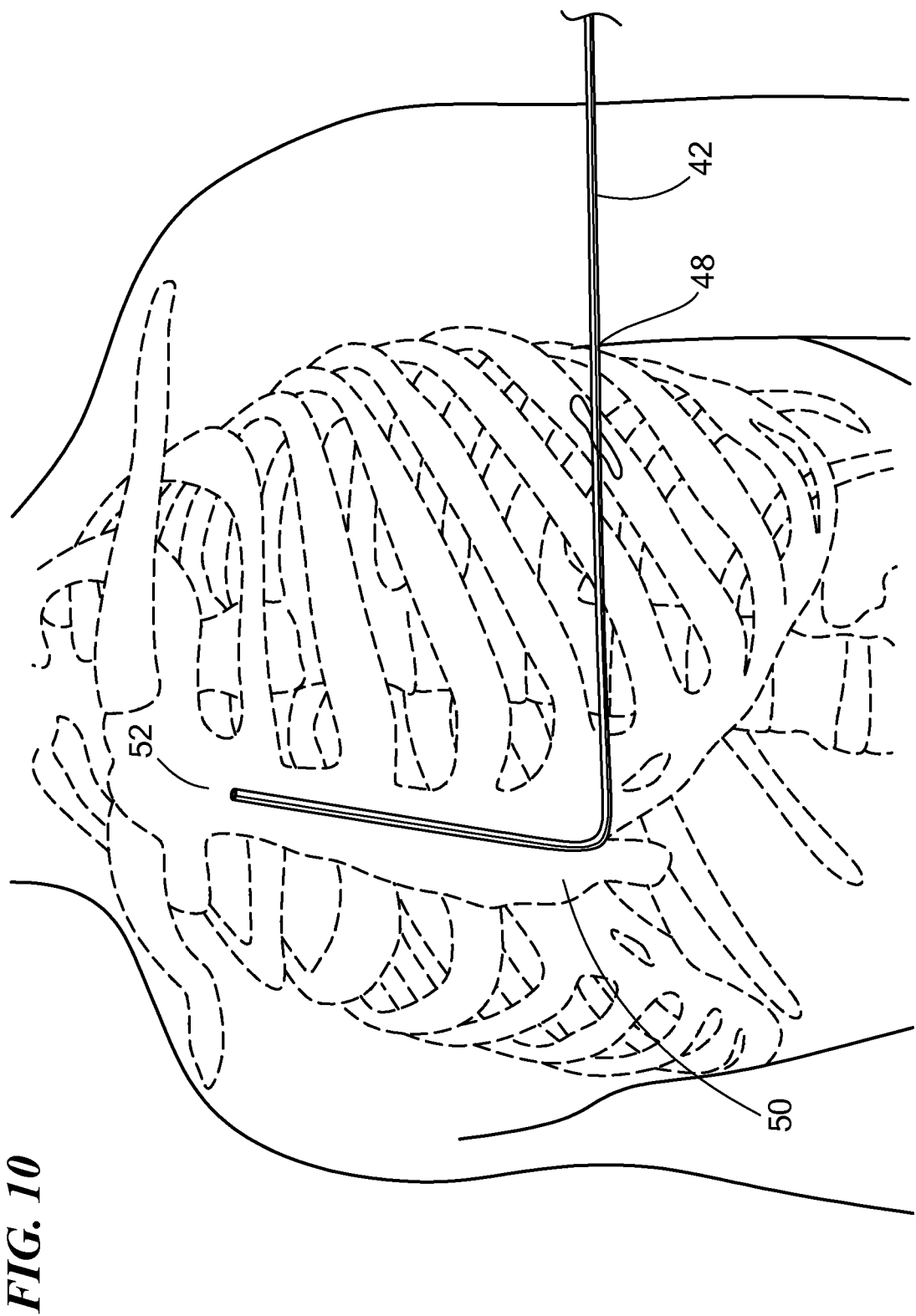
FIG. 10 is a front view of the sheath shown in FIG. 4 advanced over the first medical device and the second medical device shown in FIG. 9.

Referring now to FIG. 10, the sheath 42 may be disposed over the first medical device 12 and the second medical device 28 when the distal portion 36 of the second medical device 28 is advanced proximate the third location 52. The sheath 42 may be advanced manually by the surgeon through, for example, and introducer device, from the first incision 46 and passed the second location 50 and to the third location 52. Alternatively, the sheath may be positioned between the first medical device 12 and the second medical device 28 prior to insertion of the first medical device 12 within the patient, or the sheath may be positioned over the first medical device 12 prior to insertion of the first medical device 12 within the patient. Because the distal portion 36 is biased in a substantially rigid configuration when advanced out the distal end 16 from the second location 50 to the third location 52, when the sheath 42 is disposed over the distal portion 36 it does not cause the distal portion to dislodge or move from its position. In an exemplary configuration, the sheath 42 may extend from the first location 48 to the third location 52 and defining substantially a right angle at the second location 50.

Figure 11:
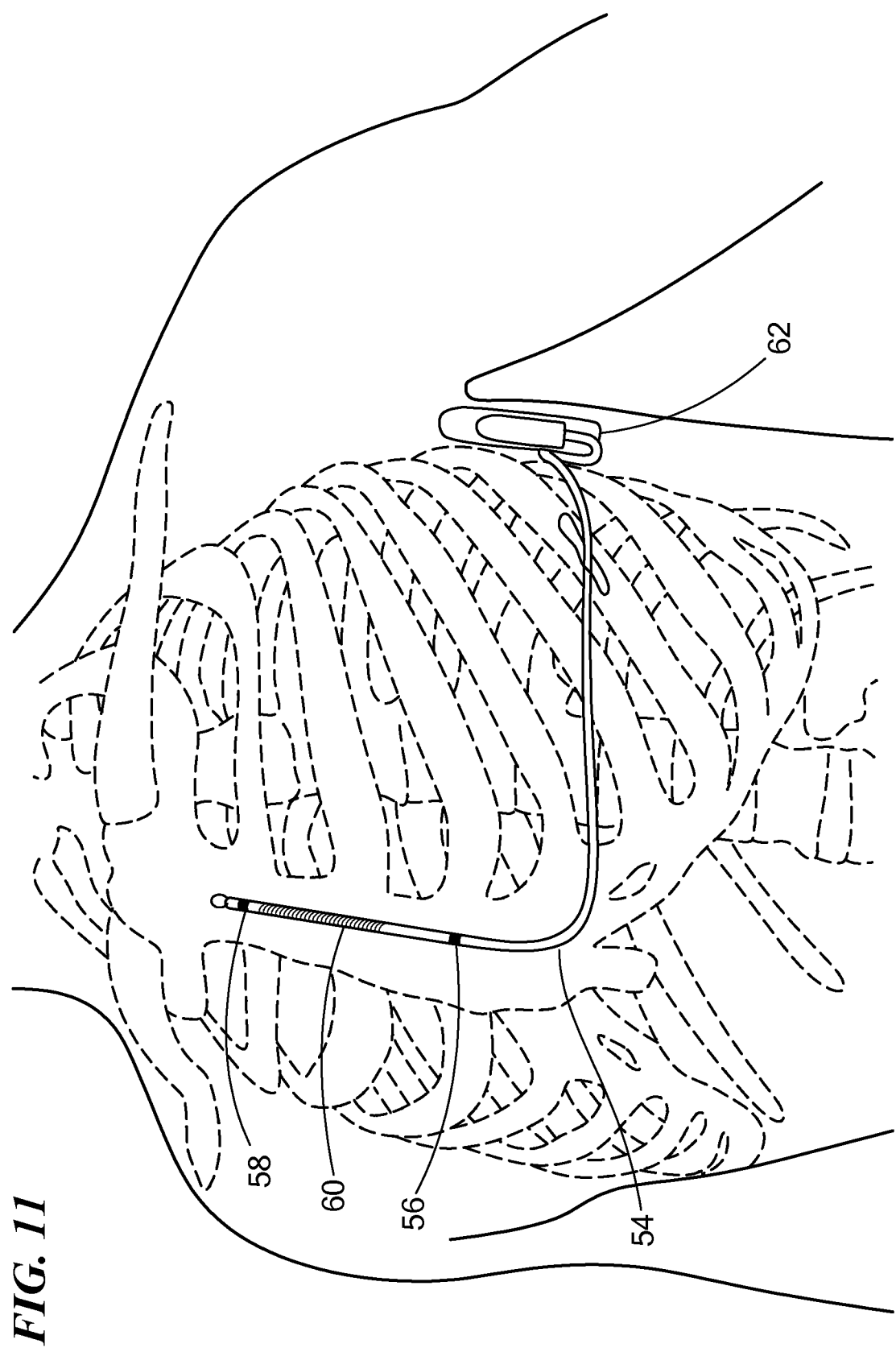
FIG. 11 is a front view of a SubQ ICD system implanted in the pathway created by the first medical device and the second medical device shown in FIG. 9.

Referring now to FIG. 11, when the sheath 42 is positioned from the first location 48 to the third location 52 as substantially shown in FIG. 10, the first medical device 12 and the second medical device 28 may be withdrawn from the patient by, for example, the surgeon manually pull on the proximal end 14 of the first medical device 12. After withdrawal of the first medical device 12 and the second medical device 28, a defibrillation lead 54 may be inserted within the sheath 42 extending from the first location 48 to the third location 52. When the surgeon has positioned the defibrillation lead 54 in the desired location, the sheath 42 may be removed from the patient by, for example, splitting the sheath along the long score 44 to separate the sheath 42 from the defibrillation lead 54. The defibrillation lead 54 may include a first electrode 56, a second electrode 58, and a third electrode 50 disposed there between. In an exemplary configuration, the first electrode 56, the second electrode 58, and the third electrode 60 may independently and/or cooperatively transmit electrical energy to heart in response to a sensed arrhythmia or other electrical malady in the heart sensed by one of more the electrodes 56, 58, and 60. The defibrillation lead 54 may further be electrically connected a housing 62 by one or more wires (not shown). The housing 62 may include an electrode, for example, a can electrode, and may further include a controller with processor and a therapy circuit (not shown) configured to measure and record electrical signals from the heart and to transmit electrical energy to the defibrillation lead 54. In an exemplary configuration, the housing 62 may be received within a pocket formed by the first incision 46. The connection between the defibrillation lead 54 and the housing 62 may operate to anchor the defibrillation lead 54 to its location superjacent the sternum.

Figure 12:
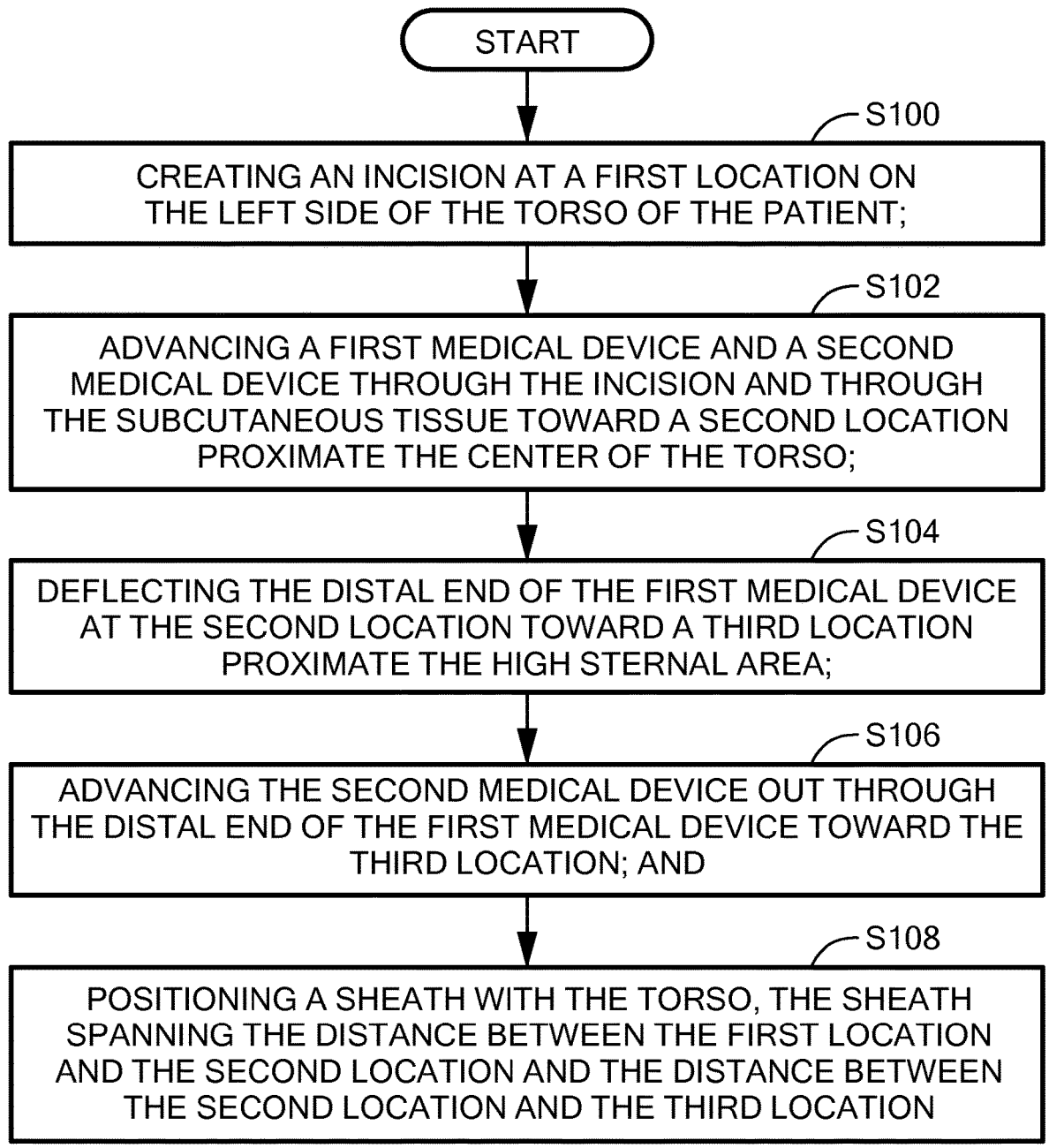
FIG. 12 is a flow diagram illustration a method of creating a pathway for insertion of a medical lead.

Referring now to FIG. 12, in an exemplary method of implanting a defibrillation in accordance with the principles described above, the method includes creating an incision 46 at a first location 48 on the left side of the torso of the patient (S100). It is further contemplated that the first location 46 may be on the right side of the torso of the patient depending on the particular anatomy of the patient. A first medical device 12 and a second medical device 28 are advanced through the incision and through the subcutaneous tissue toward a second location 50 proximate the center of the torso (S102). As discussed, any pathway may be tunneled from the first location 48 to the second location 50. The distal end 16 of the first medical device 12 is deflected at the second location 50 toward a third location 50 proximate the high sternal area. (S104). The second medical device 28 is advanced out through the distal end 16 of the first medical device 12 toward the third location 52 (S106). As discussed above, the second medical device 28 is configured to withstand bending in a radial direction when an axial force is applied on the distal end of the distal portion 26 such that the distal portion defines a substantially rigid column when advanced toward the third location 52. A sheath 42 is positioned within the torso, the sheath 42 spans the distance between the first location 48 and the second location 50 and the distance between the second location 50 and the third location 52 (S108). The sheath 24 may be positioned over the first medical device 12 prior to insertion of the second medical device 28 within the patient, between the first medical device 12 and the second medical device 28.

It will be appreciated by persons skilled in the art that the present application is not limited to what has been particularly shown and described herein above. The example embodiments described above are described in the context of a subcutaneous ICD system for purpose of illustration. However, the implant tools and techniques may also be utilized with other extravascular implanted ICD systems, such as an ICD system in which at least a portion of the lead of the implanted system is placed substernal. For example, in the exemplary use of the system 10 described in FIGS. 5-7, at the location near the xiphoid, the distal portion 36 of the second medical device 28 may be advanced in a longitudinal direction, or along any pathway, from the second location 50 to a third location underneath or below the sternum. Additionally, the tools and implant techniques of this disclosure may also be utilized with other implantable systems having implanted leads or catheters, such as implantable pacing systems, implantable neurostimulation systems, and drug delivery systems.

In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system, comprising:
   a first medical device having a first handle, a proximal end, a distal end, and a lumen therethrough, the distal end of the first medical device being deflectable; and
   a second medical device slideably receivable within the lumen of the first medical device, the second medical device having a second handle, a proximal portion, a distal portion having a major axis, the second medical device including a tube configured to create a pathway sized to receive a medical lead, the second handle sized to be received within the first handle;
   the first medical device including an actuator, the actuator including a rotatable collar configured to deflect the first medical device to an angle up to 90 degrees;
   the distal portion of the second medical device being slideable out through the distal end of the first medical device, the distal portion of the second medical device being configured to extend longitudinally at an angle substantially orthogonal to the major axis for a distance away from a distal most end of the first medical device when the distal end of the first medical device is deflected and the distal portion of the second medical device is slid out through the distal end of the first medical device; and
   the distal portion of the second medical device defines a substantially rigid longitudinal column axis when the distal end of the first medical device is deflected and the distal portion of the second medical device is slid out through the distal end of the first medical device.

2. The medical system of claim 1, further including a splittable sheath, the first medical device and the second medical device being disposed within the splittable sheath.

3. The medical system of claim 2, further including a defibrillation lead slideably receivable within the splittable sheath.

4. The medical system of claim 3, further including a can electrode in electrical communication with the defibrillation lead, the can electrode being configured to be disposed within a patient.

5. The medical system of claim 1, wherein the second medical device is configured to tunnel the pathway through subcutaneous tissue in a patient's torso.

6. The medical system of claim 1, wherein the first medical device defines a first length and the second medical device defines a second length, and wherein the second length is longer than the first length.

7. The medical system of claim 1, wherein the distal portion of the second medical device includes laser cuts.

8. The medical system of claim 1, wherein the distal portion of the second medical device is sized to span the distance between a position proximate the xiphoid process to a position proximate the second rib in the upper sternum.

* * * * *